(12) United States Patent
Fukumoto et al.

(10) Patent No.: US 8,247,002 B2
(45) Date of Patent: Aug. 21, 2012

(54) ANTIOXIDANT MATERIAL, ANTI-DETERIORATION AGENT AND FOOD OR BEVERAGE

(75) Inventors: Syuichi Fukumoto, Kasugai (JP); Kazutaka Tsuruhami, Nagoya (JP); Shigeharu Mori, Nagoya (JP)

(73) Assignees: Pokka Corporation, Aichi (JP); Amano Enzyme Inc., Aichi (JP)

( * ) Notice: Subject to any disclaimer, the term of this patent is extended or adjusted under 35 U.S.C. 154(b) by 466 days.

(21) Appl. No.: 12/379,742

(22) Filed: Feb. 27, 2009

(65) Prior Publication Data

US 2009/0175996 A1 Jul. 9, 2009

Related U.S. Application Data

(63) Continuation of application No. 11/578,849, filed as application No. PCT/JP2005/023913 on Dec. 27, 2005, now abandoned.

(30) Foreign Application Priority Data

Dec. 27, 2004 (JP) ................................ 2004-377302

(51) Int. Cl.
*A61K 36/00* (2006.01)
*A61K 36/752* (2006.01)

(52) U.S. Cl. ....................................... 424/725; 424/736

(58) Field of Classification Search .......................... None
See application file for complete search history.

(56) References Cited

U.S. PATENT DOCUMENTS

| 7,109,014 | B1 | 9/2006 | Yamamoto et al. |
| 7,118,895 | B2 | 10/2006 | Tsuruhami et al. |
| 2002/0013481 | A1 | 1/2002 | Schonrock et al. |
| 2003/0198609 | A1 | 10/2003 | Bunger |
| 2004/0081734 | A1 | 4/2004 | Lang |
| 2004/0109882 | A1 | 6/2004 | Schonrock et al. |
| 2006/0216281 | A1 | 9/2006 | Tsuruhami et al. |

FOREIGN PATENT DOCUMENTS

| JP | 11-246426 | | 9/1999 |
| JP | 11-279167 | | 10/1999 |
| JP | 2002-029975 | | 1/2002 |
| JP | 2002-355004 | | 12/2002 |
| JP | 2003-102429 | | 4/2003 |
| JP | 2004-267155 | | 9/2004 |
| JP | 2004267155 | A * | 9/2004 |
| WO | WO 00/18931 | | 4/2000 |

OTHER PUBLICATIONS

Amarume et al, Characterization and utilization of a beta-primeverosidase-like endo-beta-glycosidase from Penicillium multicolor. Glycobiology, (Nov. 2004) vol. 14, No. 11, pp. 1082.*
Miyake et al, Radical-scavenging activity in vitro of lemon peel fermented with *Aspergillus saitoi* and its suppressive effect against exercise-induced oxidative damage in rat liver. Food Science and Technology Research (2004), 10(1),70-74.*
Front page of international search report for the corresponding PCT application No. PCT/JP2005/023913 dated Mar. 16, 2006.
Front page of international search report for the corresponding PCT application No. PCT/JP2005/023913 dated Mar. 14, 2006.
Notification of Transmittal of Copies of Translation of the International Preliminary Report on Patentability (Chapter I or Chapter II of the Patent Cooperation Treaty) dated Jul. 12, 2007 in corresponding PCT application No. PCT/JP2005/023913.
Office Action issued by the U.S. Patent Office on Mar. 27, 2008 in connection with U.S. Appl. No. 11/578,849.
Office Action issued by the U.S. Patent Office on Jan. 29, 2009 in connection with U.S. Appl. No. 11/578,849.
Office Action mailed Sep. 23, 2011 in corresponding Argentina Patent Application No. P050105565 with English summary enclosed from Argentinean law firm.
Nakano, Hirofumi. "Flexibility of Glycosidases in Substrate Specificity their Possible Application to the Synthesis of Unusual Oligosaccharides and Glycosides." *Journal Appl. Glycosci.* vol. 47, No. 2 (2000): pp. 261-267. (and English abstract).
Office Action dated Sep. 7, 2010 in corresponding Japanese patent application No. 2006-550802.
Office Action dated Aug. 9, 2010 in corresponding Israeli patent application No. 178962 with English summary enclosed from Israeli law firm.

* cited by examiner

*Primary Examiner* — Qiuwen Mi
(74) *Attorney, Agent, or Firm* — Posz Law Group, PLC (57) ABSTRACT

An antioxidant material of the present invention contains flavonoid aglycon and vitamin C. The flavonoid aglycon is eriodictyol and/or diosmetin obtained by treatment of a raw material containing flavonoid glycoside derived from lemons, limes, or sudachis to form the aglycones thereof. It is preferred that this antioxidant material be produced through a step of mixing the flavonoid aglycon and the vitamin C after the treatment to form the aglycones. The treatment to form the aglycones is glycosidase treatment using a β-glycosidase derived from a microorganism of the genus *Aspergillus* or *Penicillium* multicolor, or microbial fermentative treatment using a microorganism of the genus *Aspergillus*. An anti-deterioration agent and a food or beverage of the present invention contain the antioxidant material.

6 Claims, 3 Drawing Sheets

ANTIOXIDANT MATERIAL, ANTI-DETERIORATION AGENT AND FOOD OR BEVERAGE

CROSS-REFERENCE TO RELATED APPLICATIONS

This application is a CON of application Ser. No. 11/578,849 filed on Oct. 19, 2006 now abandoned, which is a PCT National Stage patent application under 35 U.S.C. §371 of PCT/JP2005/023913 filed on Dec. 27, 2005, which in turn claims priority from JP 2004-377302 filed Dec. 27, 2004.

FIELD OF THE INVENTION

The present invention relates to an antioxidant material, an anti-deterioration agent, and a food or beverage containing the antioxidant material or the anti-deterioration agent.

BACKGROUND OF THE INVENTION

A fermented lemon is heretofore known to be obtained by subjecting at least one fermentation raw material selected from a lemon peel, segment membrane, and pulp to microbial fermentative treatment using *Aspergillus saitoi* (see Patent Document 1). This fermented lemon is produced through a reaction that generates 8-hydroxyhesperetin by the microbial transformation of hesperidin contained in the fermentation raw material. This fermented lemon exhibits high antioxidative effects and can readily encourage the increasing and effective use of lemons. Alternatively, Patent Document 2 discloses a fermented lemon obtained by subjecting a fermentation raw material consisting of a lemon fruit or a part thereof to microbial fermentative treatment using *Aspergillus niger* or *Aspergillus awamori*.

[Patent Document 1] Japanese Laid-Open Patent Publication No. 2002-355004
[Patent Document 2] Japanese Laid-Open Patent Publication No. 2003-102429

SUMMARY OF THE INVENTION

The present inventors have developed, by intensive studies, an antioxidant material that exhibits antioxidative effects higher than the effects expected from conventional fermented lemons, and have consequently achieved this invention. A first object of the present invention is to provide an antioxidant material that easily exhibits high antioxidative effects and an anti-deterioration agent that easily exhibits high inhibitory effects on deterioration. A second object of the present invention is to provide a food or beverage that easily exhibit high antioxidative effects and inhibitory effects on deterioration.

For attaining the first object, one aspect of the present invention provides an antioxidant material containing a flavonoid aglycon (aglycone) and vitamin C. The flavonoid aglycon is eriodictyol and/or diosmetin obtained by treatment of a raw material containing flavonoid glycoside derived from lemons, limes, or sudachis to form the aglycones thereof.

For attaining the first object, an alternative aspect of the present invention provides an antioxidant material containing flavonoid aglycon. The flavonoid aglycon is eriodictyol and/or diosmetin obtained by glycosidase treatment of a raw material containing flavonoid glycoside derived from lemons, limes, or sudachis using a β-glycosidase derived from *Penicillium* multicolor.

For attaining the first object, a further alternative aspect of the present invention provides an anti-deterioration agent containing the antioxidant material.

For attaining the second object, a further alternative aspect of the present invention provides a food or beverage containing the antioxidant material or the anti-deterioration agent.

DESCRIPTION OF THE PREFERRED EMBODIMENTS

The following provides a detailed explanation of an embodiment of the present invention.

An antioxidant material of the embodiment contains flavonoid aglycon (hereinafter, referred to as aglycon) derived from citrus, for example, lemons, limes, or sudachis, and vitamin C (ascorbic acid) as effective ingredients. This antioxidant material exhibits useful effects, for example, exceedingly high antioxidative and inhibitory effects on deterioration, by the synergistic effects of the aglycon and the vitamin C. The aglycon is obtained by treatment of a raw material containing flavonoid glycoside derived from the citrus to form the aglycones thereof.

It is preferred that this antioxidant material be produced through a mixing step of mixing the aglycon obtained by the treatment to form the aglycones with the vitamin C. However, when the vitamin C content in the raw material is as high as in lemon fruit and a reduction in vitamin C caused by the treatment to form the aglycones can be suppressed, it is less necessary to perform the mixing step. Namely, this antioxidant material needs to contain vitamin C in at least an amount detectable with a detection device known in the art and, preferably, contains vitamin C that is mixed in the mixing step. In a method for producing this antioxidant material, processing steps (e.g., diluting, condensing, extracting, purifying, and drying steps) other than the step of subjecting the flavonoid glycoside to the treatment to form the aglycones and the mixing step may be performed.

This antioxidant material contains the effective ingredients that exhibit high antioxidative effects. The antioxidant material can exhibit, for example, a high effect for promoting health by suppressing the oxidative degeneration of biocomponents caused by active oxygen. The antioxidant material is contained for use in, for example, food or beverage (health food), pharmaceuticals, quasi-drugs, and cosmetics. Moreover, the antioxidant material can effectively suppress various kinds of deterioration of products, for example, the oxidative deterioration of fats and oils, the deterioration of flavor components, the decomposition of pigments, and the fading of pigments. Since this antioxidant material contains the effective ingredients that exhibit high antioxidative effect, it is particularly preferred that the antioxidant material be contained for use in food or beverage such as health food. The food or beverage include beverage products or food products such as isotonic beverage s, tea beverage s, tea leaves, herbs, dairy products (e.g., milk and yogurt), food products containing gelling agents (e.g., pectin and carrageenan), excipients (e.g., lactose and dextrin), flavor components, sweeteners, and fats and oils. The food or beverage can be processed into various shapes and utilized as, for example, tablets, powders, granules, or capsules and can also be utilized as syrup or candy.

Eriodictyol and/or diosmetin are used as the aglycon. Preferably, eriodictyol is used because of exhibiting high antioxidative effects. These aglycones are obtained by subjecting flavonoid glycoside contained in raw material containing leaves or fruits of the citrus, or a component of the fruit to form the aglycones thereof. The flavonoid glycoside has a structure where aglycon and sugar are bonded by a glycoside linkage. Namely, the aglycon is generated (liberated) by enzyme reaction (glycosidase reaction) that cleaves the glycoside linkage of the flavonoid glycoside. In this enzyme reaction, sugar is simultaneously generated (liberated) as a by-product.

Any of substance containing leaves or fruits of the citrus, or a portion of a component of the fruit is used as the raw material. Preferably, a flavonoid glycoside extract drawn from a component other than juice of the citrus is used. Alternatively, juice of the citrus or flavonoid glycoside purified (isolated) from the extract may be used as the raw material. Preferably, a hydrophilic solvent, for example, water, alcohol (methanol or ethanol), and hydrous alcohol, is used as a solvent for obtaining the extract. More preferably methanol, an aqueous solution thereof, or water, still more preferably, water is used because water can be obtained at low prices. A citrus fruit mainly consists of juice, a peel (albedo and flavedo), a segment membrane, and pulp. Because citrus leaves and fruit have an aglycon content of less than 0.01% by weight, they hardly contain aglycon. In addition, for reasons of saving time required for producing the raw material and easy promotion of effective use of fruit of the citrus, it is most preferred that a squeezed juice residue of fruit of the citrus from which juice has already been squeezed, or an extract thereof be used as the raw material. The squeezed juice residue contains a peel (albedo and flavedo), a segment membrane, a portion of pulp, and a trace amount of juice left unsqueezed and especially contains a large amount of the flavonoid glycoside.

The flavonoid glycoside has a structure where the aglycon and monosaccharide or disaccharide are bonded by a glycoside linkage. Examples of this flavonoid glycoside include: eriocitrin or eriodictyol-7-glucoside, glycoside composed of eriodictyol and rutinose (L-rhamnosyl-D-glucose); diosmin or diosmetin-7-glucoside, glycoside composed of diosmetin and rutinose; and 6,8-di-C-β-glucosyldiosmin (DGD) or 6-C-β-glucosyldiosmin (GD), glycoside composed of diosmetin and glucose. These flavonoid glycosides have high antioxidative effect. On the other hand, the aglycon includes eriodictyol or diosmetin. These aglycones have antioxidative effect and in-vivo absorbability significantly improved as compared with those of the flavonoid glycoside. Of these two aglycones, eriodictyol, which has been shown to exhibit especially high antioxidative effect, is more preferably used.

When a raw material that contains vitamin C in large amounts is subjected to form the aglycones thereof, the vitamin C is hardly reduced by the treatment to form the aglycones and remains in the antioxidant material. Therefore, when the treatment to form the aglycones is performed using a fruit, roughly purified flavonoid glycoside, or juice that contains vitamin C, the resulting aglycon can exhibit the synergistic effect with the vitamin C without undergoing the mixing step of mixing vitamin C separately prepared with the aglycon. In such a case, it is preferred that the fruit of the citrus should be subjected directly to form the aglycones thereof. It is also preferred that the roughly purified flavonoid glycoside should be subjected to form the aglycones thereof, or otherwise, a raw material composed of the fruit or the roughly purified flavonoid glycoside supplemented with juice should be subjected to form the aglycones thereof. On the contrary, when the aglycon with high purity is required, it is preferred that highly purified flavonoid glycoside with high purity should be subjected to form the aglycones thereof.

The treatment to form the aglycones includes microbial fermentative treatment or glycosidase treatment.

The microbial fermentative treatment is treatment conducted by inoculating the raw material with a microorganism of the genus *Aspergillus* and culturing the microorganism under given fermentation conditions for a given period. This microbial fermentative treatment liberates aglycon from flavonoid glycoside by β-glycosidase produced by the microorganism (especially, a vegetative hypha). Examples of the microorganism include black-koji mold and yellow-koji mold. Examples of the black-koji mold include *Aspergillus saitoi*, *Aspergillus niger*, and *Aspergillus awamori*. Examples of the yellow-koji mold include *Aspergillus oryzae*, *Aspergillus sojae*, and *Aspergillus tamarii*. Of these microorganisms, preferably the black-koji mold, particularly preferably *Aspergillus niger* or *Aspergillus awamori* is used because of its excellent reaction efficiency of conversion to aglycon.

A method for inoculating the raw material with the microorganism includes a method in which spores of the microorganism is directly sprinkled and attached to the raw material. Alternatively, the following inoculation is also possible. The inoculation is achieved by conducting preculture treatment where a medium containing the microorganism is cultured with shaking in advance under aerobic conditions. The precultured medium is then sprinkled and attached to the entire raw material. Alternatively, the raw material is immersed into the precultured medium. The microbial fermentative treatment is easily performed under aerobic conditions. Therefore, it is preferable to use a culture container with a wide bottom and a shallow depth, for example, a culture dish having a closed bottom, in the microbial fermentative treatment. Preferably, the raw material is uniformly placed to spread throughout the inside bottom of the culture container. A fermentation temperature is preferably 10 to 40° C., more preferably 20 to 40° C., on account of being suitable conditions for the growth of the microorganism. Preferably, the microbial fermentative treatment is performed in the dark on account of this being suitable conditions for the growth of the microorganisms.

For performing the treatment to form the aglycones further specifically and efficiently, it is preferred that conditions for this microbial fermentative treatment be adjusted as follows. The microbial fermentative treatment is carried out with a vegetative hypha of the microorganism of the genus *Aspergillus* in a state of high β-glycosidase activity and low activity of the other enzymes (e.g., hydroxylase). The conditions mainly include a fermentation period. The fermentation period for obtaining the aglycon in large amounts is terminated, preferably before the completion of spore formation of the vegetative hypha of the microorganism, more preferably at some point in time during the spore formation, still more preferably at the start of the spore formation. When the preculture treatment is performed, the fermentation period is preferably 2 to 12 days, more preferably 2 to 8 days, still more preferably 3 to 7 days. If this fermentation period is less than 2 days, a sufficient amount of the aglycon is not generated. On the other hand, if the fermentation period exceeds 12 days, the generated aglycon might be decomposed or modified, leading to a reduced yield of the aglycon. When the preculture treatment is not performed, the fermentation period is preferably 1 to 3 weeks, more preferably 1 to 2 weeks.

A fermented product obtained by the microbial fermentative treatment is much more fragile and likely to crumble, because the decomposition of its fiber proceeds due to fermentation. Solid contents, for example, the unfermented raw material whose fiber is insufficiently decomposed due to fermentation still in progress and mycelia of the inoculated strain formed during fermentation, are present in this fermented product. Volume of the solid contents is approximately one tenth of that of the raw material before the microbial fermentative treatment.

When the aglycon in this fermented product is purified, solid content removal treatment for removing the solid contents mainly composed of the inoculated microorganism and the unfermented raw material is initially performed. This solid content removal treatment is a treatment in which the solid contents are removed by immersing the fermented product that contains the solid contents in a polar solvent to transfer and extract the aglycon into the solvent. The solvent is then filtrated with gauze, a rough mesh, or the like. Alternatively this solid content removal treatment is a treatment in which the solid contents are removed by lightly centrifuging the solution (e.g., centrifugation on the order of 2000×g for 30 minutes). When the fermented product is extracted in a polar solvent, the extraction temperature is preferably room temperature (25° C.) and an extraction time is preferably 2 hours or more, for achieving high extraction efficiency.

Preferably, methanol, ethanol, an aqueous solution thereof, or water is used as the polar solvent. Alternatively, it is also possible to use lower alcohol (e.g., butanol and isopropanol) or an aqueous solution thereof as the polar solvent. It is preferred to use methanol, an aqueous solution thereof, or water as this polar solvent, because cost for treating a large amount of the fermented product is low. It is most preferred to use water because purification cost is low. For killing the microorganism to terminate microbial fermentation, it is preferred to use methanol, ethanol, or an aqueous solution thereof with a high concentration (e.g., 20% or more by volume).

In addition, fiber component removal treatment for separating and removing a water-soluble fiber component mainly composed of pectin contained in the fermented product can be performed after the solid content removal treatment. This fiber component removal treatment is treatment in which the fiber component is removed by centrifuging the fermented product that has undergone the solid content removal treatment to precipitate the water-soluble fiber component to the inside bottom of a centrifugal tube or the like. In this fiber component removal treatment, the fermented product is centrifuged with centrifugal force on the order of 11000×g for 20 minutes in the case of using methanol or ethanol as the polar solvent. Additionally, the fermented product is centrifuged at centrifugal force stronger than the above-described centrifugal force in the case of using water or an aqueous solution as the polar solvent.

On the other hand, the glycosidase treatment is treatment in which an enzyme reaction that cleaves a glycoside linkage of flavonoid glycoside contained in the raw material is performed by the action of β-glycosidase on the raw material. In this enzyme reaction, the aglycon as well as sugar as a by-product is generated from the flavonoid glycoside in the raw material. In this glycosidase treatment, it is preferred that the enzyme reaction be performed by adding β-glycosidase to an extract (extracted solution) of a component of a citrus fruit other than juice, or citrus juice in order to enhance the efficiency of the treatment. Alternatively, in the glycosidase treatment, the enzyme reaction may be performed by bringing an immobilizing carrier therein into contact with the juice or the extract for the β-glycosidase enzyme activity. A condensed or diluted solution of the citrus juice may be used as the above-described citrus juice.

Preferably, the β-glycosidase (hereinafter, referred to as first glycosidase) produced by the microorganism of the genus *Aspergillus* or β-glycosidase (hereinafter, referred to as second glycosidase) produced by *Penicillium* multicolor is used as the above-described β-glycosidase.

The first glycosidase is glycoside hydrolase (heterosidase) and has enzyme activity that cleaves a β-1,6 linkage between the aglycon and D-glucose constituting the flavonoid glycoside. The first glycosidase also has, for example, enzyme activity that liberates p-nitrophenol (pNP) when reacted with para-nitrophenyl-β-D-glucopyranoside (pNPG), glycoside serving as a substrate.

It is possible to use, as the first glycosidase, any enzyme purified from either a culture supernatant or a disrupted cell mass (vegetative hyphae or spores) of the microorganism of the genus *Aspergillus* used as starting material by utilizing a color developed from pNP during the decomposition of the substrate as a marker. Alternatively, the direct use of a culture supernatant of the microorganism of the genus *Aspergillus*, or a disrupted cell mass of the microorganism from which insoluble matter has been removed is most convenient. When the culture supernatant is used in the glycosidase treatment, it is particularly preferred to use the first glycosidase derived from *Aspergillus awamori, Aspergillus shirousamii*, or *Aspergillus japonicus* because its activity in the culture supernatant of any such species is significantly higher. It is most preferred to use a culture supernatant or a disrupted cell mass at the time of the start of spore formation of the microorganism of the genus *Aspergillus* because the activity of the first glycosidase is significantly higher. It is preferred to use a cell mass grown in a medium with a high content of the flavonoid glycoside, preferably in a carbohydrate-free medium.

In the glycosidase treatment using the first glycosidase, treatment temperature is preferably 10 to 60° C., more preferably 20 to 40° C., still more preferably 30 to 40° C., on account of easily enhancing the activity of the first glycosidase. Treatment time is preferably 1 to 24 hours, more preferably 1 to 12 hours, still more preferably 2 to 6 hours. Although pH at the time of the glycosidase treatment is preferably 2 to 9, more preferably 4 to 8, still more preferably 5 to 6, it may fall within a pH range (approximately pH 2.5 to 3.5) shown by, for example, the citrus juice and a solution of the squeezed juice residue.

The second glycosidase is glycoside hydrolase and has an enzyme activity that cleaves a β-1,6 linkage between the aglycon and D-glucose constituting the flavonoid glycoside. The second glycosidase also has enzyme activity that generates eriodictyol-7-glucoside and subsequently eriodictyol from eriocitrin and generates diosmetin-7-glucoside and subsequently diosmetin from diosmin. Namely, the second glycosidase has the property of rutinose-decomposing enzyme that cleaves a β-1,6 linkage between L-rhamnose and D-glucose. Moreover, the second glycosidase has, for example, enzyme activity that liberates pNP when reacted with para-nitrophenyl-β-primeveroside (pNPP), glycoside serving as a substrate.

It is possible to use, as the second glycosidase, any of those purified from a culture supernatant or a disrupted cell mass of

*Penicillium* multicolor used as starting material by utilizing a color developed from pNP during the decomposition of the substrate pNPP as a marker. Alternatively, the direct use of a culture supernatant of *Penicillium* multicolor, or a disrupted cell mass of the microorganism (*Penicillium* multicolor) from which insoluble matter has been removed is most convenient. It is preferred to use such a cell mass grown in a medium with a high content of the substrate or the flavonoid glycoside, preferably in a carbohydrate-free medium.

In the glycosidase treatment using the second glycosidase, treatment temperature is preferably 10 to 70° C., more preferably 40 to 60° C., on account of easily enhancing the activity of the second glycosidase. In light of the stability of the enzyme with respect to temperature, the treatment temperature is most preferably a temperature on the order of 50° C. at which the most stable treatment effect can be obtained most efficiently. Treatment time is preferably 0.2 to 24 hours, more preferably 0.5 to 2 hours. Although pH at the time of the glycosidase treatment is preferably 2 to 9, more preferably 4 to 8, still more preferably 6 to 8, on account of easily enhancing the activity of the second glycosidase, it may fall within a pH range (approximately pH 2.5 to 3.5) shown by, for example, the citrus juice and a solution of the squeezed juice residue.

When the first and second glycosidases are added to the raw material, it is preferred that the glycosidases be inactivated or removed after the completion of the glycosidase treatment. On the other hand, the antioxidant material having an enhanced content of the aglycon can be obtained easily by purifying (condensing) the flavonoid glycoside in advance by use of an adsorbent before the above-described treatment to form the aglycones. Preferably, a synthetic adsorbent, for example, Amberlite XAD manufactured by Organo is used as the adsorbent. Alternatively, the antioxidant material having an enhanced content of the aglycon can be obtained easily by purifying (condensing) the aglycon by use of the adsorbent after the treatment to form the aglycones. The purification with the adsorbent may be performed for recovering the flavonoid glycoside present in the antioxidant material due to insufficient enzyme treatment. Furthermore, the purification with the adsorbent has an advantage that impurities in the raw material can be removed effectively.

A first food or beverage (health food) as food or beverage of the embodiment contains the antioxidant material. The effective ingredients, that is, the aglycon and vitamin C, of the antioxidant material exhibit high antioxidative effects. Therefore, the first food or beverage exhibits, for example, high effects for promoting health by suppressing the oxidative degeneration of biocomponents caused by active oxygen. It is preferred that the first food or beverage be ingested orally with several doses (2 to 3 doses or more) per day. It is particularly preferred that one ingest a first food or beverage when in a state likely to be exposed to oxidative stress, for example, before and after vigorous workouts, when exposed to stress, and before and after smoking.

When adults ingest the first food or beverage, the aglycon is ingested at preferably 0.1 to 10 g, more preferably 0.5 to 2 g, per day. In the first food or beverage, if the amount of the aglycon ingested is less than 0.1 g per day, antioxidative effects by the effective ingredients might not be enhanced effectively. On the other hand, it is uneconomical to ingest the aglycon in an amount exceeding 10 g. In the case of children, the amount of the aglycon ingested is adjusted depending mainly on their body weights, and as a guide, is half the amount for adults. Likewise, when adults ingest the first food or beverage, the vitamin C is ingested at preferably 0.1 to 10 g, more preferably 0.1 to 2 g per day. In the first food or beverage, if the amount of the vitamin C ingested is less than 0.1 g per day, antioxidative effects by the effective ingredients might not be enhanced effectively. On the other hand, it is uneconomical to ingest the vitamin C in an amount exceeding 10 g. Moreover, concentration of the vitamin C contained in the first food or beverage is preferably 10 ppm or higher, more preferably 100 ppm to 0.5% by weight, still more preferably 1000 ppm to 0.3% by weight. If the concentration is less than 10 ppm, the vitamin C does not effectively produce the synergistic effect with the aglycon, whereas it is uneconomical to use the vitamin C with a concentration exceeding 0.5% by weight.

An anti-deterioration agent of the embodiment contains the antioxidant material. The effective ingredients, that is, the aglycon and vitamin C, of the antioxidant material exhibit high inhibitory effects on deterioration. Therefore, the anti-deterioration agent effectively suppresses various kinds of deterioration of products, for example, the oxidative deterioration of fats and oils, the deterioration of flavor components, the decomposition of pigments, and the fading of pigments. This anti-deterioration agent is utilized as an oxidative anti-deterioration agent for fats and oils against thermal deterioration and oxidative deterioration of vegetable oil, fish oil, and the like. Additionally, this anti-deterioration agent is utilized as an anti-deterioration agent for flavor components against thermal deterioration and oxidative deterioration of flavor components. This anti-deterioration agent is also utilized as a fading inhibitor for pigments against thermal deterioration and deterioration from light of natural pigments.

A second food or beverage as food or beverage of the embodiment contain the anti-deterioration agent and have a preservative property enhanced by the effective ingredients. The second food or beverage may be produced by adding vitamin C, for example, to food or beverage containing the aglycon or a material thereof, or on the contrary, by adding the aglycon, for example, to food or beverage containing vitamin C or a material thereof. The second food or beverage includes fat and oil products, flavor products, and products supplemented with pigments. Content of the aglycon in the second food or beverage is preferably 10 ppm or higher, more preferably 100 ppm to 0.5% by weight, still more preferably 1000 ppm to 0.3% by weight. If the content is less than 10 ppm, the second food or beverage might not sufficiently produce inhibitory effects on deterioration, whereas the use of the aglycon at a content exceeding 0.5% by weight is uneconomical and might considerably change the taste and flavor of the food or beverage. On the other hand, concentration of the vitamin C contained in the second food or beverage is the same as in the first food or beverage.

Advantages produced by the embodiments will be described below.

The antioxidant material of the embodiment contains the aglycon derived from citrus and vitamin C as effective ingredients. Therefore, this antioxidant material can be utilized in a wide range of applications, for example, health food, pharmaceuticals, quasi-drugs, cosmetics, antioxidants, and active oxygen-eliminating agents, because of high antioxidative effects produced by the effective ingredients. In this context, the aglycon exhibits excellent in-vivo absorbability, especially when orally ingested, and high antioxidative effects and therefore easily exhibits high effects for promoting health. When this antioxidant material is contained for use in pharmaceuticals, quasi-drugs, or cosmetics, the amounts of the aglycon and the vitamin C ingested, administered, or used per day are preferably the same as the amounts of the aglycon and the vitamin C ingested in the description of the above-described food or beverage. This antioxidant material can also effectively suppress the oxidative deterioration of fats and oils, the deterioration of flavor of flavor components, and the decomposition or fading of pigments. Therefore, this antioxidant material can be added to food or beverage containing fats and oils, flavor components, or pigments, thereby easily enhancing the preservative property of the food or beverage. Furthermore, this antioxidant material has effects for suppressing both thermal deterioration and deterioration from light by itself and as such, is exceedingly useful and economical.

Especially, when vitamin C with a concentration not lower than 500 ppm, more preferably 1000 ppm, which is higher than that of vitamin C contained in citrus juice, is contained in the antioxidant material and the food or beverage, antioxidative effects are synergistically enhanced with ease. In general, the vitamin C is also contained in a raw material containing flavonoid glycoside and however, is removed during the course of purification of the aglycon. Accordingly, the vitamin C can be mixed with the purified aglycon, thereby producing significantly high antioxidative effects.

The aglycon is generated easily and properly by subjecting flavonoid glycoside derived from a citrus to form the aglycones thereof (glycosides treatment or microbial fermentative treatment). In the glycosidase treatment, the aglycon can be generated with exceedingly high efficiency from the flavonoid glycoside by using the second glycosidase derived from *Penicillium* multicolor. Namely, the second glycosidase has significantly high substrate specificity and enzyme reactivity for particular flavonoid glycoside (eriocitrin or diosmin) contained in large amounts in lemons, limes, and sudachis, as compared with those of commercially available enzymes (enzymes known in the art). Therefore, the second glycosidase can generate the aglycon with exceedingly high efficiency. For this reason, the use of the second glycosidase easily enhances the rate of conversion of the flavonoid glycoside to the aglycon. Therefore, the aglycon can be produced easily in large amounts. In addition, production cost can be reduced easily.

On the other hand, in the microbial fermentative treatment using the above-described conventional fermented lemon, hesperidin (glycoside) is hydrolyzed to hesperetin (aglycon). Then, modification reaction that adds a hydroxyl group to the hesperetin proceeds as the fermentative treatment is further continued. Therefore, uncertain reaction against flavonoid glycoside other than the hesperidin, for example, analogous modification reaction and reaction that decomposes the glycoside, is highly likely to be caused under conditions for the microbial fermentative treatment for producing the conventional fermented lemon. Accordingly, it was difficult to obtain aglycon of interest at high yields. By contrast, in the present embodiment, the microbial fermentative treatment is initiated by inoculating the raw material with spores or hyphae of a microorganism of the genus *Aspergillus* and terminated before the completion of subsequent spore formation of the microorganism. Thereby, in the present embodiment, microbial transformation mainly by vegetative hyphae of the microorganism is easily performed. Therefore, the aglycon is easily obtained at high yields by terminating the microbial fermentative treatment before modification reaction such as hydroxylation reaction, or decomposition reaction proceeds. In general, it is almost impossible to generate the aglycon only by squeezing juice from a citrus fruit or by extraction from the fruit. In addition, it is almost impossible to generate the aglycon in processing steps other than the treatment to form the aglycones.

A large amount of flavonoid glycoside can be obtained with great ease by using a squeezed juice residue of a citrus fruit from which juice has already been squeezed as compared with using citrus juice. Alternatively, a large amount of flavonoid glycoside can be obtained with great ease by using a flavonoid glycoside extract drawn from the squeezed juice residue as the raw material containing flavonoid glycoside as compared with using citrus juice. Since a large amount of the squeezed juice residue is put into disposal when, for example, beverage containing the citrus juice is produced, the squeezed juice residue is available at exceedingly low prices. In addition, the use of the squeezed juice residue is more preferred in light of Food Recycling Law.

The second food or beverage has a significantly excellent preservative property because of high inhibitory effect on decomposition produced by the effective ingredients in the antioxidant material. Therefore, this food or beverage can suppress a reduction in quality with significant effectiveness. Accordingly, it is possible to store them over a further longer period, and it is also possible to set a new quality preservation period that is greatly extended. This contributes much to cost reduction because the amounts of food or beverage disposal that is disposed of beyond the quality preservation period be reduced with great ease. Quality preservation after the production of the food or beverage needs to depend less on, for example, temperature control at low temperatures. On the other hand, this food or beverage contains the effective ingredients derived from a natural product and have significantly excellent in-vivo absorbability. Therefore, the food or beverage is easy to use as food additives.

Example 1

Sample Preparation 1: Production of Aglycon by Glycosidase Treatment

A squeezed juice residue of a lemon was immersed in a 10 fold amount (by weight) of methanol for 24 hours to thereby obtain a lemon flavonoid glycoside extract. The obtained extract was condensed under reduced pressure with an evaporator and then adsorbed to Amberlite resin (XAD16; manufactured by Organo) to remove pectin, carbohydrate, and so on as much as possible. An eluate eluted therefrom with 40% hydrous methanol was condensed and freeze-dried to thereby obtain a lemon flavonoid glycoside mixture powder (lemon glycoside of Comparative Example 1). This powder contains approximately 30% eriocitrin and approximately 2 to 5% diosmin. This lemon glycoside of Comparative Example 1 was dissolved in water, and eriocitrin was purified using HPLC Fractionation System 1 described below under HPLC Condition 1 described below. The purified eriocitrin was then condensed and freeze-dried to thereby obtain an eriocitrin powder (eriocitrin of Comparative Example 2).

<HPLC Fractionation System 1>

Pump: Shimadzu LC-8A, System Controller: Shimadzu SCL-8A, Autoinjector: Shimadzu SIL-8A, Detector: Shimadzu SPD-8A (UV spectrophotometric detector), Fraction Collector: Shimadzu FCV-100B <HPLC Condition 1>

Column: YMC-Pack ODS-A (50 i.d.×250 mm), Eluent: methanol/water=50/50 (v/v), Flow Rate: 100 ml/min, Detection Wavelength: 270 nm (Glycosidase Treatment of Eriocitrin and Diosmin)

The eriocitrin of Comparative Example 2 or diosmin manufactured by Wako Pure Chemical Industries was dissolved at a final concentration of 5 mM in 20 mM sodium acetate-hydrochloric acid buffer. A glycoside solution whose pH was adjusted to 3.0 by the buffer and a glycoside solution whose pH was adjusted to 5.0 by the buffer were produced.

Because the diosmin is refractory to water, the glycoside solution was produced after the diosmin was dissolved in advance in dimethyl sulfoxide. These glycoside solutions were supplemented with 100 ppm or 10 ppm of β-glycosidase (second glycosidase) to produce reaction solutions, which were in turn subjected to glycosidase treatment with stirring with a stirrer at approximately 30° C. The β-glycosidase is an enzyme with β-primeveroside-decomposing enzyme activity, which has been purified from a *Penicillium* multicolor IAM 7153 strain by the present inventors by utilizing a color developed from pNP as a marker, and has β-glycosidase activity of 173 units/g. One unit defines the amount of enzyme capable of hydrolyzing pNPP to liberate 1 µmol of pNP at 30° C. for 1 minute. Several-milliliter aliquots were sampled from the reaction solutions after 0, 0.5, 1, 2, 4, 5, and 8 hours after the addition of the second glycosidase. The samples were heated at 95° C. for 10 minutes to inactivate the enzyme. The resulting samples were rapidly cooled and cryopreserved. The obtained samples were analyzed using HPLC Analysis System 2 described below under HPLC Condition 2 to confirm changes in the concentration of each substance caused by the glycosidase treatment. The results are shown in FIGS. 1 to 4.

<HPLC Analysis System 2>

Pump: Shimadzu LC-10AD, System Controller: Shimadzu SCL-10A, Autoinjector: Shimadzu SIL-10A, Detector: Shimadzu SPD-10A (UV spectrophotometric detector), Column Oven: Shimadzu CTO-10A <HPLC Condition 2>

Column: YMC-Pack ODS-A (4.6 i.d.×250 mm), Eluent: methanol/water=40/60 (v/v), Flow Rate: 1 ml/min, Detection Wavelength: 270 nm As seen in FIGS. 1 to 4, a rapid decrease in concentration was observed in both eriocitrin (FIGS. 1 and 2) and diosmin (FIGS. 3 and 4) immediately following the addition of the second glycosidase, and the generation of their respective aglycones, eriodictyol and diosmetin, was confirmed. Conversion rates as high as approximately 50 to 60% for the conversion of eriocitrin to eriodictyol and approximately 80% for the conversion of diosmin to diosmetin were obtained. This result showed that the present enzyme promoted conversion to aglycon with exceedingly high efficiency without loss. Conversion to aglycon was confirmed to proceed with almost the same efficiency in the solution of pH 5.0 that fell within the optimum pH range of the second glycosidase, and in the solution of pH 3.0 with almost the same efficiency. For example, the pH of lemon, lime, and sudachi juices and the pH of the extracted flavonoid glycoside solution are in the vicinity of 3. Therefore, it was confirmed that the enzyme activity of the present enzyme was hardly impaired in the lemon, lime, and sudachi juices or a solution of flavonoid glycoside obtained from any of them, and the present enzyme could be utilized in these solutions. Even when 10 ppm of the second glycosidase was added, conversion to aglycon was shown to sufficiently proceed by spending enough time. In the treatment described below, investigation was conducted in consideration of treatment time, with the addition of 10 ppm of β-glycosidase per mM substrate as a guide.

(Conversion of Lemon Flavonoid to Aglycon and Purification Thereof)

The lemon glycoside of Comparative Example 1 was dissolved at a final eriocitrin concentration of 1 mM in 20 mM sodium acetate-hydrochloric acid buffer. A glycoside solution whose pH was adjusted to 3.0 by the buffer and a glycoside solution whose pH was adjusted to 5.0 by the buffer were produced. These glycoside solutions were supplemented with 10 ppm of the second β-glycosidase to produce reaction solutions, which were in turn subjected to glycosidase treatment with stirring with a stirrer at approximately 30° C. Several-milliliter aliquots were sampled from the reaction solutions after 0, 0.5, 1, 2, 4, 5, and 8 hours after the addition of the second glycosidase. The samples were heated at 95° C. for 10 minutes to inactivate the enzyme. The resulting samples were rapidly cooled and cryopreserved. The obtained samples were analyzed under HPLC Condition 1 described above to confirm changes in the concentration of each substance caused by the glycosidase treatment. The results are shown in FIGS. 5 and 6.

Figure 1:
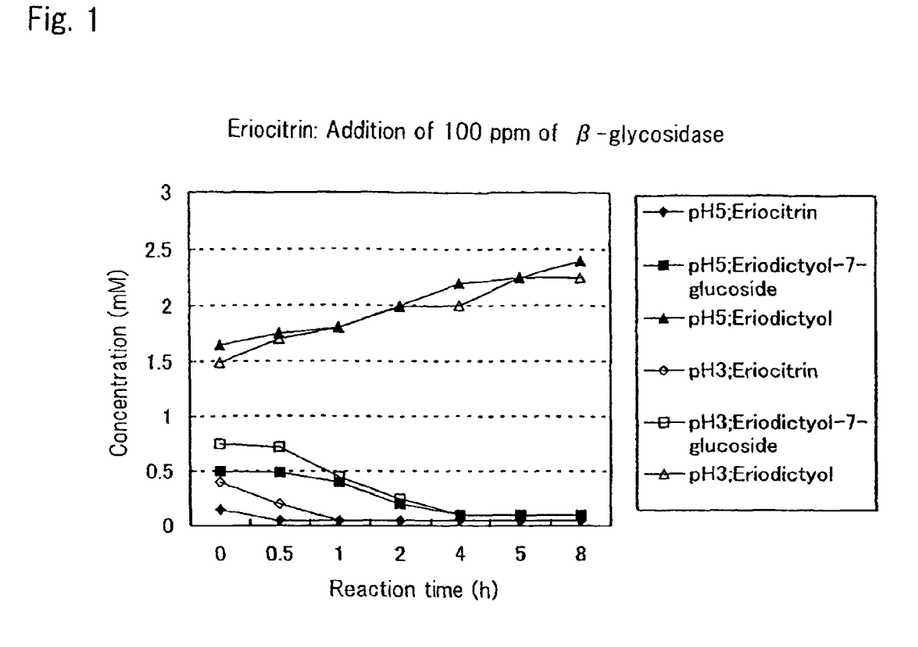
FIG. 1 is a graph showing changes in the concentrations of eriocitrin and so on in Example 1 of the present invention.
Figure 2:
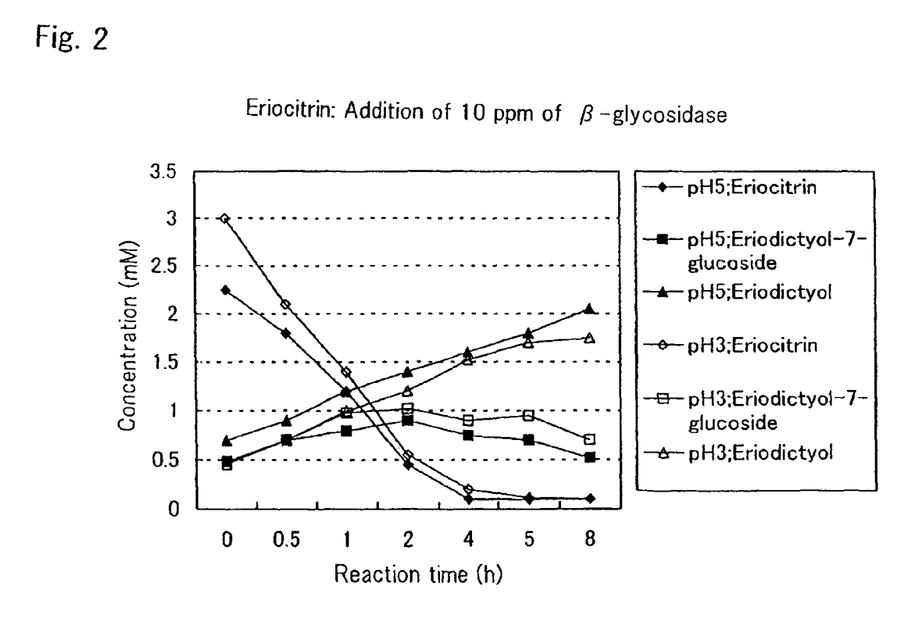
FIG. 2 is a graph showing changes in the concentrations of eriocitrin and so on in Example 1.
Figure 3:
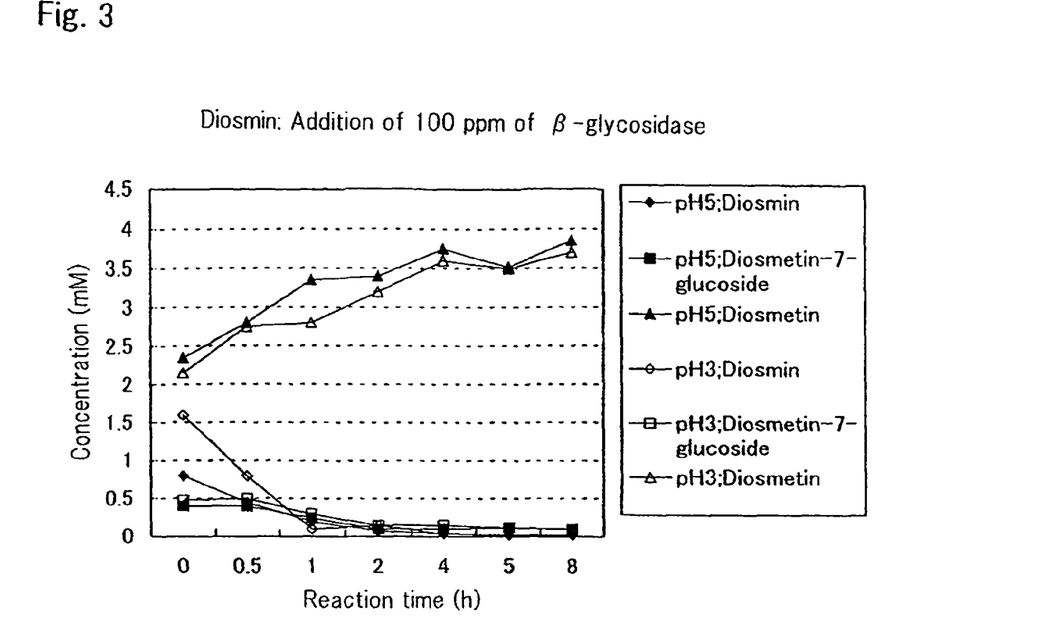
FIG. 3 is a graph showing changes in the concentrations of diosmin and so on in Example 1.
Figure 4:
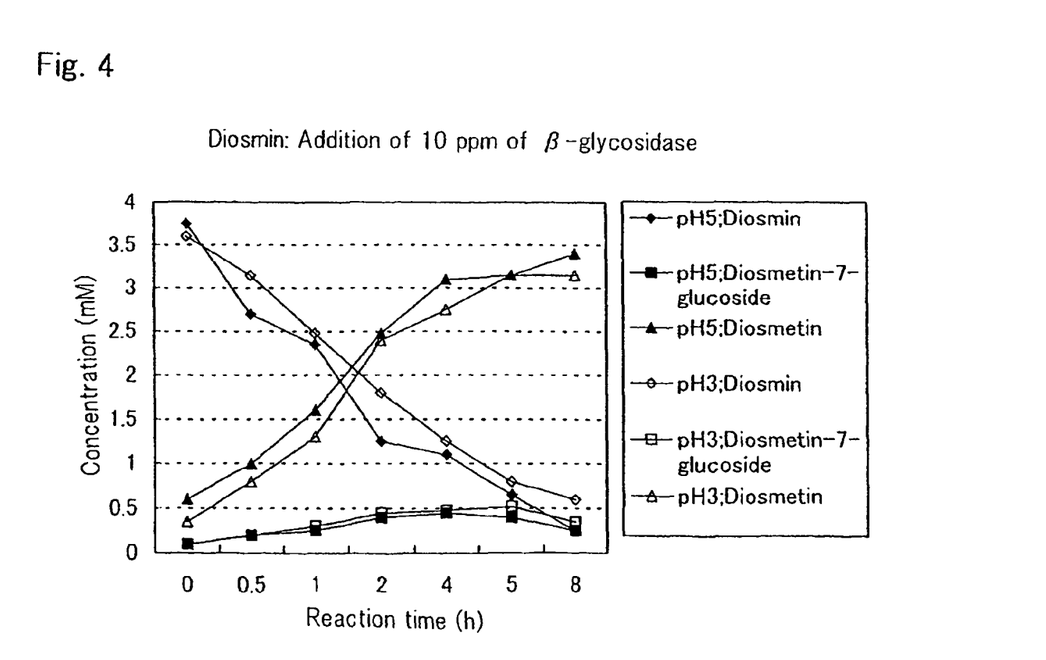
FIG. 4 is a graph showing changes in the concentrations of diosmin and so on in Example 1.
Figure 5:
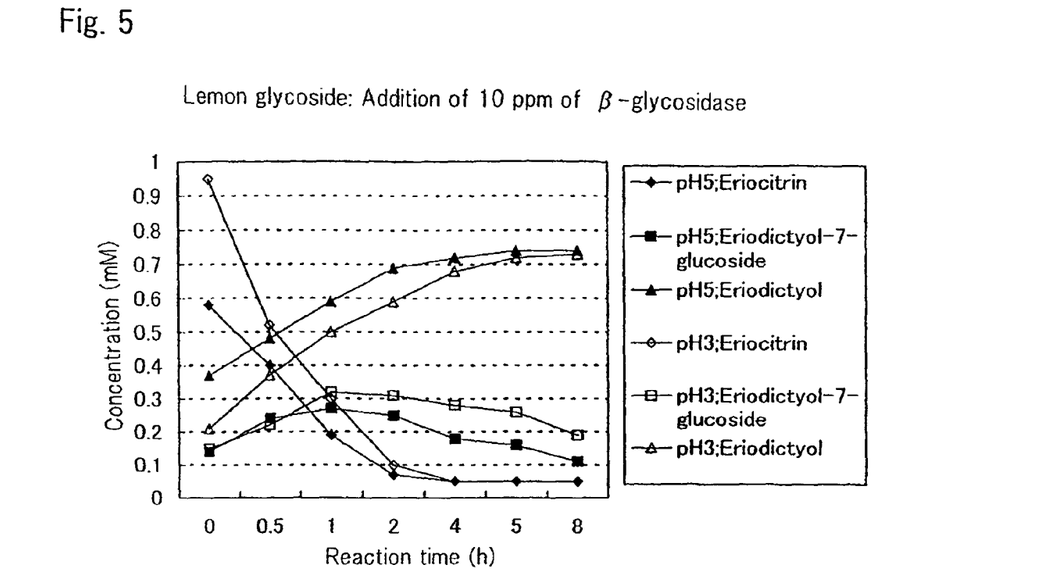
FIG. 5 is a graph showing changes in the concentrations of eriocitrin and so on in Example 1.
Figure 6:
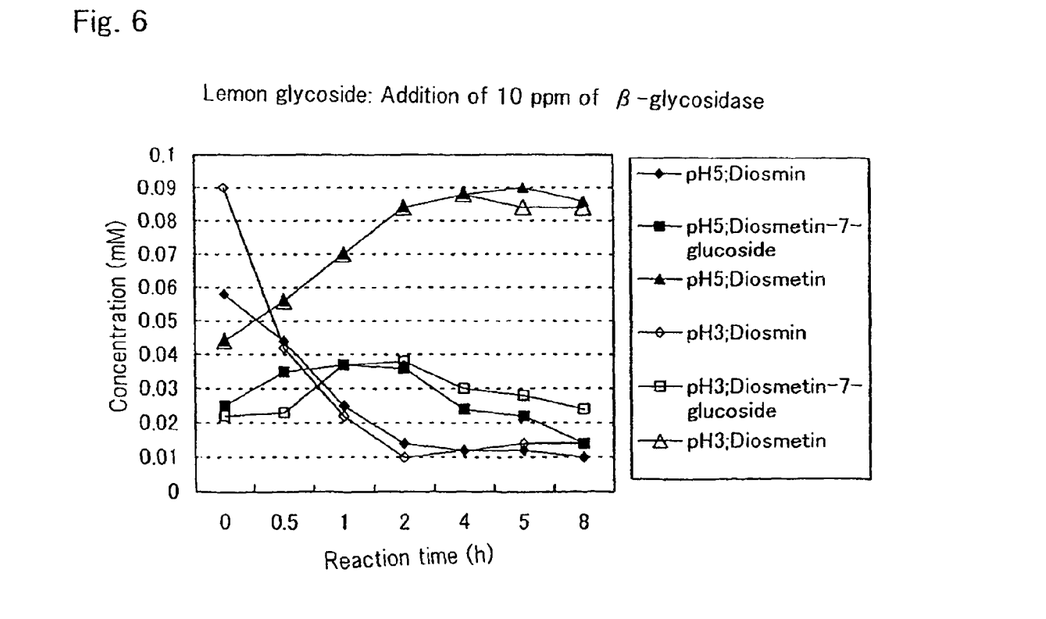
FIG. 6 is a graph showing changes in the concentrations of diosmin and so on in Example 1.

As seen in FIGS. 5 and 6, both eriocitrin and diosmin, flavonoid glycosides extracted from a lemon, were confirmed to exhibit a high rate of conversion close to 70% by the treatment conducted for approximately 2 hours. A decrease in enzyme activity depending on pH was not observed. Therefore, it was also confirmed that the treatment of lemon glycoside was in no need of pH adjustment. Next, the reaction solution (pH 3.0) after 8 hours after the addition of the second glycosidase was adsorbed to the Amberlite resin. An eluate eluted therefrom with 60% hydrous methanol was freeze-dried (enzyme-treated aglycon of Test Example 1). This eluate (enzyme-treated aglycon of Test Example 1) was analyzed under HPLC Condition 2 described above to thereby investigate the degree of purification of the aglycon. As a result, it was confirmed that the aglycon was purified exceedingly effectively by the purification with the adsorbent.

(Investigation of Substrate Specificity of Enzyme)

For confirming the usefulness of the second glycosidase, a test was conducted on conversion to aglycon using commercially available enzymes. The enzymes used were 4 enzymes of cellulase-based enzymes (Cellulase A "Amano" 3 and Cellulase T "Amano" 4) and pectinase-based enzymes (Pectinase G "Amano" and Pectinase PL "Amano") manufactured by Amano Enzyme as well as the second glycosidase. The lemon glycoside of Comparative Example 1 was dissolved at its concentration of 50 ppm in a solvent to produce an aqueous solution (whose pH was adjusted to 3.0). The aqueous solution was in turn supplemented with 500 ppm or 50 ppm of each of the enzymes to undergo enzyme reaction at room temperature (25° C.) for 5 hours. Each of these samples that had undergone the enzyme reaction was heated at 95° C. for 10 minutes to inactivate the enzyme. Eriocitrin and eriodictyol concentrations in the resulting samples were quantified under HPLC Condition 2 described above to determine a rate of conversion of eriocitrin. As a result, when 500 ppm of Pectinase PL "Amano" was added, the rate of conversion of eriocitrin to eriodictyol was 22%, whereas when 500 ppm and 50 ppm of the second glycosidase were added, the rate of conversion was 67% and 74%, respectively. In the other tests, the rate of conversion was almost 0%. Thus, the rate of conversion by the second glycosidase was confirmed to be much higher than the rate of conversion by the commercially available enzymes.

(Glycosidase Treatment of Citrus Juice)

Lemon, lime, and sudachi juices with high eriocitrin content were supplemented with the second glycosidase and investigated for conversion to aglycon. These 3 juices and commercially available concentrated juice were used and respectively adjusted to Brix 10. The pH of all the juices was in the vicinity of 3. The second glycosidase was added at a final concentration of 10 ppm to these juices to perform enzyme reaction at room temperature for 5 hours. Each of these samples that had undergone the enzyme reaction was heated at 95° C. for 10 minutes to inactivate the enzyme. Eriocitrin and eriodictyol concentrations in the resulting samples were quantified under HPLC Condition 2 described above to determine a rate of conversion of eriocitrin. As a result, the rate of conversion of eriocitrin to eriodictyol was 54%, 49%, and 56% in the lemon juice, the lime juice, and the sudachi juice, respectively, and was confirmed to be high in these juices. Thus, the second glycosidase was confirmed to be useful in conversion to aglycon for these citrus juices.
(Measurement of Radical-Scavenging Activity)

Each sample shown in Table 1 described below was examined for DPPH (1,1-diphenyl-2-picrylhydrazyl) radical-scavenging activity. Namely, the lemon glycoside of Comparative Example 1, the eriocitrin of Comparative Example 2, the enzyme-treated aglycon of Test Example 1, or eriodictyol, neoeriocitrin, vitamin C, or α-tocopherol purchased from Funakoshi was dissolved at its concentration of 500 ppm in a solvent to produce an aqueous solution. Then, 100 μl aliquot of the aqueous solution was supplemented with 1 ml of 0.1 M Tris buffer (pH 7.4). The solvent used for α-tocopherol was methanol. Alternatively, each sample described above and vitamin C were dissolved at each concentration of 500 ppm in a solvent to produce an aqueous solution whose 100 μl aliquot was then supplemented with 1 ml of 0.1 M Tris buffer. Subsequently, 2 ml of a DPPH solution (solution obtained by dissolving DPPH at its concentration of 500 μM in ethanol) was added to the solutions and well mixed. The resulting solutions were left at room temperature for 20 minutes in the dark to undergo reaction. The amount of DPPH in each reaction solution (10 μl) was quantified by measurement using HPLC Analysis System 2 described below under HPLC Condition 3. In a method of evaluating radical-scavenging activity, the amount of DPPH remaining in the sample (glycoside and aglycon)-free test section (control) was regarded in advance as 100%. Additionally, the amount of DPPH remaining in the reaction solution supplemented with each sample was measured and indicated by percentage (%) with respect to the amount of DPPH in the control section. Because the radical-scavenging activity of the section supplemented with eriodictyol and vitamin C was almost 100%, the test was conducted again with the amount of the sample reduced to half. Namely, eriodictyol and vitamin C were dissolved at each concentration of 500 ppm in a solvent to produce an aqueous solution whose 50 μl aliquot was then supplemented with 1 ml of 0.1 M Tris buffer. The radical-scavenging activity of the resulting solution was measured as described above. The obtained numeric value was doubled to thereby correct the data. The result is shown in Table 1.

<HPLC Analysis System 2>

Pump: Shimadzu LC-10AD, System Controller: Shimadzu SCL-10A, Autoinjector: Shimadzu SIL-10A, Detector: Shimadzu SPD-10A (UV spectrophotometric detector), Column Oven: Shimadzu CTO-10A <HPLC Condition 3>

Column: TSK-GEL octyl-80Ts (4.6 i.d.×150 mm), Eluent: methanol/water=30/70 (v/v), Flow Rate: 1 ml/min, Detection Wavelength: 517 nm

TABLE 1

|  | DPPH radical-scavenging activity | Rate of inhibition against oxidation of methyl linoleate |
|---|---|---|
| Control | 0.00% | 0.00% |
| Lemon glycoside | 6.18% | 7.11% |
| Lemon glycoside + vitamin C | 24.18% | 17.59% |
| Enzyme-treated aglycon | 15.97% | 14.19% |
| Enzyme-treated aglycon + vitamin C | 35.91% | 25.44% |
| Eriocitrin | 28.64% | 8.00% |
| Eriocitrin + vitamin C | 51.09% | 18.77% |
| Eriodictyol | 75.70% | 20.99% |
| Eriodictyol + vitamin C | 101.10% | 32.53% |
| Neoeriocitrin | 30.70% | 9.24% |
| Vitamin C | 14.00% | 8.32% |
| α-tocopherol | 44.82% | 16.97% |

As seen in Table 1, the enzyme-treated aglycon, the eriocitrin, and the eriodictyol had high antioxidative activity mainly under conditions of water systems. The antioxidative activity of the enzyme-treated aglycon, the eriocitrin, and the eriodictyol was remarkably enhanced in the sections supplemented with them mixed with vitamin C. Furthermore, it was shown that the antioxidative activity of the enzyme-treated aglycon, the eriocitrin, and the eriodictyol was also synergistically enhanced in the lemon glycoside by mixing them with vitamin C. Purified eriocitrin or eriodictyol supplemented with vitamin C exhibited synergistic effect at almost the same rate as that of the lemon glycoside or the enzyme-treated aglycon supplemented with vitamin C. Accordingly, it was confirmed that the synergistic effect observed in the lemon glycoside and the enzyme-treated aglycon was attributed to the synergistic effect of eriocitrin or eriodictyol and vitamin C. Thus, an antioxidant material in which any of these flavanones was mixed with vitamin C was shown to have exceedingly high antioxidative activity and to be useful as an antioxidant material that suppresses deterioration caused by oxidation. When the enzyme-treated aglycon or, for the purpose of inhibiting deterioration, eriodictyol was added to food or beverage containing vitamin C, for example, juice, it can readily be supposed that the food or beverage can be expected to have inhibitory effects on deterioration stronger than the inhibitory effects on deterioration expected from the amounts of them added.

(Measurement of Inhibitory Effects on Generation of Peroxide Lipid)

Each sample shown in Table 1 described above was examined for inhibitory effects on the generation of peroxide lipid, with methyl linoleate as a substrate. Namely, 100 μl of each aqueous solution used in the paragraph (Measurement of radical-scavenging activity) and 89 mg (100 μl) of methyl linoleate were added to a small test tube of 14 mm in inner diameter and well mixed. At the same time, 100 μl of only the solvent for the aqueous solution was added instead of the aqueous solution to prepare a control. The solvents in these mixture solutions were completely removed in a vacuum desiccator using a vacuum pump. The resulting solutions were left in the dark at 40° C. for 18 hours. Next, 5 ml of 0.08% BHT (2,6-di-t-butyl-4-methylphenol)/hexane solution was added thereto. The amount of peroxide generated from methyl linoleate was measured using HPLC Analysis System 2 shown below under HPLC Condition 4. In a method of measuring and evaluating antioxidative activity, the total of HPLC peak area of peroxide lipids (13-hydroperoxide and 9-hydroperoxide) generated from methyl linoleate in the control test section was determined first. This determined value was regarded as 100%. The total HPLC peak area of the peroxide lipids in the test section supplemented with each sample was determined. This determined value was indicated by percentage (%) with respect to the total of HPLC peak area of the control to thereby determine a rate of inhibition against the oxidation of methyl linoleate. The result is shown in Table 1 described above.

<HPLC Analysis System 2>

Pump: Shimadzu LC-10AD, System Controller: Shimadzu SCL-10A, Autoinjector: Shimadzu SIL-10A, Detector: Shimadzu SPD-10A (UV spectrophotometric detector), Column Oven: Shimadzu CTO-10A <HPLC Condition 4>

Column: Develosil ST 60-5 (4.6 i.d.×250 mm), Eluent: n-hexane/1,4-dioxane/isopropylalcohol=98/1/1 (v/v/v), Flow Rate: 1 ml/min, Detection Wavelength: 235 nm As seen in Table 1 described above, the lemon glycoside, the enzyme-treated aglycon, the eriocitrin, and the eriodictyol had high antioxidative activity mainly under conditions of oil systems. The antioxidative activity of the lemon glycoside, the enzyme-treated aglycon, the eriocitrin, and the eriodictyol was synergistically exerted in the sections supplemented with them mixed with vitamin C. Purified eriocitrin or eriodictyol supplemented with vitamin C exerted synergistic effect at almost the same rate as that of the lemon glycoside or the enzyme-treated aglycon supplemented with vitamin C. Accordingly, it was confirmed that the synergistic effects observed in the lemon glycoside and the enzyme-treated aglycon was attributed to the synergistic effects of eriocitrin or eriodictyol and vitamin C. Thus, an antioxidant material in which any of these flavanones was mixed with vitamin C was shown to have exceedingly high antioxidative activity and be useful as an antioxidant material that suppresses deterioration caused by oxidation.

(Verification of Inhibitory Effect on Oxidation of Biomembrane Using Liposome)

A single compartment liposome (SUV: Small Unilamellar Vesicle) was used as a biomembrane model to evaluate antioxidative power. For preparing SUV, at first, 100 mg of yolk lecithin was supplemented with 1 ml of chloroform and completely dissolved, followed by the complete removal of the chloroform in a short-neck flask. The obtained lipid film was swollen by the addition of 10 ml of 10 mM phosphate buffer (pH 7.4) containing 500 ppm of the lemon glycoside of Comparative Example 1, the eriocitrin of Comparative Example 2, the enzyme-treated aglycon of Test Example 1, or eriodictyol (manufactured by Funakoshi). The resulting mixture was well shaken and completely dispersed with an ultrasonic washing machine. The lipid film swollen by the addition of 10 ml of only the phosphate buffer was tested as a control in the same way. Next, the obtained multilayer liposome solution was bubbled with nitrogen gas for 5 minutes and then sonicated at 180 W for 20 minutes in a strong ultrasonic generator to prepare a small unilamellar vesicle (SUV).

The peroxidation of the SUV thus prepared was forcedly promoted by the addition of AAPH (2,2'-azobis(2-aminodipropane)), a radical initiator, to the SUV. As a result, a peroxide as a primary product is generated in the liposome. Subsequently, as a secondary product such as malondialdehyde is generated during the course of autoxidation. A thiobarbituric acid (TBA) reagent is added thereto to generate a red substance (TBA-positive substance), a reaction product of aldehydes. The degree of coloration thereof was measured with a spectrophotometer at $\lambda=535$ nm and used to determine the rate of oxidation of the liposome membrane (%).

As a result, the rate of oxidation of the liposome membrane was 60.54% for the lemon glycoside of Comparative Example 1, while the rate of oxidation of the liposome membrane was 11.56% for the enzyme-treated aglycon of Test Example 1. Accordingly, the enzyme-treated aglycon was shown to produce high antioxidative activity. The rate of oxidation was 76.87% for α-tocopherol. The rate of oxidation of the liposome membrane was 9.52% and 6.80% for the eriocitrin of Comparative Example 2 and the eriodictyol, respectively. Thus, lemon aglycon and eriodictyol were shown to exert a high antioxidative effect in a biomembrane and to be useful as a biomembrane oxidation inhibitor that eradicates the oxidative injury of the surfaces of cell membranes in organisms.

(Measurement of Rate of Elimination of Active Oxygen)

Xanthine oxidase (0.5 ml (5.6 units)) was mixed with 0.3 ml of 1 mM xanthine (manufactured by Wako Pure Chemical Industries), 0.3 ml of 0.25 mM nitro blue tetrazolium (manufactured by Wako Pure Chemical Industries), and 2.3 ml of 0.05 M sodium carbonate buffer (pH 10.2). The xanthine oxidase used was a reagent (manufactured by Wako Pure Chemical Industries) diluted at 100 fold with 0.05 M sodium carbonate buffer. This mixture was supplemented with 0.1 ml (concentration: 1000 ppm) of the lemon glycoside of Comparative Example 1 or the enzyme-treated aglycon of Test Example 1 and incubated. Because blue formazan was produced with a lapse of incubation time, absorbance at $\lambda=560$ nm was measured using a spectrophotometer (HITACHI spectrophotometer U2000) after 3 minutes of incubation. A test section without addition of the sample (glycoside and aglycon) was used as control. As a blank test, a sodium carbonate buffer was added instead of the xanthine oxidase to perform the same procedures. A value obtained by subtracting the absorbance of the blank test from the absorbance of the solution supplemented with each sample was divided by the absorbance of the control to thereby determine a rate of elimination of active oxygen (%). As a result, the rate of elimination of active oxygen was 26.7% for the lemon glycoside of Comparative Example 1, while the rate of elimination of active oxygen was 74.8% for the enzyme-treated aglycon of Test Example 1. Accordingly, the enzyme-treated aglycon was shown to produce high antioxidative activity. The rate of oxidation was 238.2% for α-tocopherol. Thus, lemon aglycon was shown to have high ability for eliminating active oxygen and to be useful as an in-vivo active oxygen-eliminating agent.

Example 2

Sample Preparation 2: Production of Aglycon by Microbial Fermentative Treatment

An *Aspergillus saitoi* IAM 2210 strain precultured in advance at 30° C. for 1 week in a potato dextrose broth medium in the dark was inoculated on a squeezed juice residue of lemons to perform microbial fermentative treatment under constant temperature conditions at 30° C. for 10 days. Then, the squeezed juice residue of a lemon containing the strain was immersed in 10 fold (by weight) of methanol for 24 hours to thereby obtain a lemon aglycon extract. The obtained extract was condensed under reduced pressure with an evaporator and then adsorbed to Amberlite resin (XAD16) to remove pectin, carbohydrate, and so on as much as possible. An eluate eluted therefrom with 40% hydrous methanol was condensed and freeze-dried to thereby obtain a fermentation-treated lemon aglycon powder (fermentation-treated aglycon of Comparative Example 3). The composition (content) of flavonoid contained in each of the lemon glycoside of Comparative Example 1 and the fermentation-treated aglycon of Comparative Example 3 was analyzed using HPLC Analysis System 2 described below under HPLC Condition 5 described below. The result is shown in Table 2. In Table 2, "trace" means that the substance could hardly be detected under HPLC Condition 5 described below, and "nd" means that the substance was undetectable under HPLC Condition 5 described below.

<HPLC Analysis System 2>

Pump: Shimadzu LC-10AD, System Controller: Shimadzu SCL-10A, Autoinjector: Shimadzu SIL-10A, Detector: Shimadzu SPD-10A (UV spectrophotometric detector), Column Oven: Shimadzu CTO-10A <HPLC Condition 5>

Column: YMC-Pack ODS-A (4.6 i.d.×250 mm), Eluent: methanol/water=30/70 (v/v), Flow Rate: 1 ml/min, Detection Wavelength: 270 nm

TABLE 2

|  | Lemon glycoside (Comparative Example 1) | | Fermentation-treated aglycon (Comparative Example 3) | |
|---|---|---|---|---|
| Eriocitrin | 716.0 mg | 1.20 mM | 113.7 mg | 0.19 mM |
| Narirutin | 29.7 mg | 0.05 mM | trace | — |
| Hesperidin | 213.0 mg | 0.35 mM | 41.9 mg | 0.07 mM |
| Eriodictyol | trace | — | 175.8 mg | 0.61 mM |
| Naringenin | nd | — | 5.1 mg | 0.02 mM |
| Hesperetin | trace | — | 41.4 mg | 0.14 mM |

Content per 100 g of powder (Measurement of β-Glycosidase Activity in Culture Supernatant)

Each strain shown in Table 3 described below was subjected to preculture treatment at 30° C. for 2 weeks in a potato dextrose broth medium in the dark. The medium in the time of the start of spore formation was centrifuged to collect the resulting culture supernatant, which was in turn used as enzyme solution sample 1. Alternatively, following preculture treatment at 30° C. for 4 weeks in the dark, the medium in the time of the completion of spore formation was centrifuged to separate a culture supernatant from a precipitate. The culture supernatant was used as enzyme solution sample 2. In addition, the precipitate was suspended by the addition of water thereto in the same amount as that of the culture supernatant and sonicated to thereby disrupt the cells. The resulting disrupted cells mass from which insoluble matter had been removed by centrifugation was used as enzyme solution sample 3.

Next, 2 ml of 1 mM pNPG solution dissolved in 0.1 M phosphate-citrate buffer (pH 5.0) was dispensed into a test tube and prewarmed at 30° C. for 5 minutes in a constant temperature water bath. A 0.5 ml aliquot of each of the enzyme solution samples was added to this test tube to undergo enzyme reaction. The amount of pNP generated was measured using a spectrophotometer (HITACHI spectrophotometer U2000) at λ=420 nm. As a control, the substrate pNPG solution was supplemented in advance with a sodium carbonate solution and subsequently with each enzyme solution sample to perform the same procedures. The amount of the enzyme generating 1 μmol of pNP per hour under this condition was regarded as 1 unit. β-glycosidase activity (unit) in the 0.5 ml aliquot of each of the enzyme solution samples was determined from a calibration curve constructed in advance with a pNP standard solution according to a calculation formula described below. The result is shown in Table 3.

β-glycosidase activity (unit)=absorbance (420 nm)/0.223 (unit)

TABLE 3

| Strain | Enzyme solution sample | | |
|---|---|---|---|
|  | 1 | 2 | 3 |
| A. awamori RIB 2804 | 1.53 | 1.71 | 1.81 |
| A. shirousamii IAM 2414 | 1.79 | 1.15 | 1.32 |
| A. shirousamii RIB 2503 | 0.02 | 0.54 | 0.50 |
| A. usamii RIB 2001 | 0.05 | 1.27 | 1.04 |
| A. niger ATCC 10549 | 0.07 | 1.03 | 1.54 |
| A. niger ATCC 38857 | 0.02 | 1.79 | 1.53 |
| A. japonicus ATCC 20236 | 0.93 | 1.24 | 1.40 |
| A. saitoi IAM 2210 | 0.00 | 1.70 | 1.89 |

All measurements are in the shown above units.

As seen in Table 3, almost all of the strains were shown to have strong β-glycosidase activity attributable to the first glycosidase in the time of the completion of spore formation (enzyme solution samples 2 and 3). Because the A. awamori and A. shirousamii IAM 2414 strains had strong β-glycosidase activity in the culture supernatant in the time of the start of spore formation (enzyme solution sample 1), it was revealed that the culture solutions of these strains could be utilized as enzymes for glycosidase treatment by sterilization and filtration. Because, for example, hydroxylase activity is exceedingly weak in this time at the start of spore formation, the decomposition and additional microbial transformation reaction of the generated aglycon are less likely to proceed. Therefore, it is possible to obtain the aglycon more efficiently. When microbial fermentative treatment is performed using these A. awamori and A. shirousamii IAM 2414 strains, it can easily be supposed that its microbial fermentation period can be shortened with ease as compared with using other strains. On the contrary, it was also revealed that strains such as the A. niger strains (especially, ATCC 10549), which showed less β-glycosidase activity extracellularly but had high activity intracellularly, was suitable for use in microbial fermentative treatment.

(Test of Inhibitory Effect on Deterioration of Flavor Component)

An aqueous solution adjusted to Brix 4.8 and pH 3.0 by use of glucose and citric acid was supplemented with 0.1% of a lemon essence (manufactured by Takasago International) to prepare a syrup solution. A sample-supplemented or sample-free section of this syrup solution with or without addition of the lemon glycoside of Comparative Example 1, the fermentation-treated aglycon of Comparative Example 4 (indicated by aglycon in Table 4), or vitamin C was prepared. These sections were subjected to flash pasteurization by heating to 87° C. and then packed into clear, colorless PET bottles. The lemon glycoside of Comparative Example 1 was added so that its eriocitrin concentration was brought to the added concentration shown in Table 4. The fermentation-treated aglycon of Comparative Example 4 was also added so that its eriodictyol concentration was brought to the added concentration shown in Table 4. Moreover, as to whether or not the addition of the fermentation-treated aglycon of Comparative Example 4 affected the flavor of the whole syrup solution was examined, the addition of eriodictyol at 30 ppm or less did not largely affect the flavor. The sample for each of these sections was used to conduct deterioration tests by warming and ultraviolet radiation as described below.

Deterioration Test by Warming: Test 1-1 (30 ppm) and Test 1-2 (3 ppm)

A sample of each section was left undisturbed and stored at 60° C. or 4° C. (refrigeration) for 4 days in the dark, followed by sensory evaluation by 12 well-trained panelists. In an evaluation method, the panelists evaluated the respective scores of the sections, with the sample stored by refrigeration rated as the maximum score of 5, to determine an average score thereof. Four sensory evaluation tests were all performed by the same panelists on the same day. The result is shown in Table 4.

Deterioration Test by Ultraviolet Radiation: Test 2-1 (30 ppm) and Test 2-2 (3 ppm)

A sample of each section was stored by refrigeration under ultraviolet (UV) radiation conditions (6-hour radiation) with an ultraviolet long life fade-o-meter (manufactured by Suga Test Instruments) or in the dark, followed by sensory evaluation by 12 well-trained panelists. In an evaluation method, the panelists provided the respective scores for the sections, with the sample stored in the dark rated defined as having the maximum score of 5, to determine an average score thereof. Four sensory evaluation tests were all performed by the same panelists on the same day. The result is shown in Table 4.

significant difference was observed in sensory evaluation by the panelists. These results showed that the addition of eriocitrin or eriodictyol at a concentration of 3 ppm or higher to the syrup solution produced significant inhibitory effect on the deterioration of flavor caused by heating, and the addition of eriocitrin or eriodictyol simultaneously with vitamin C remarkably enhanced the effect.

On the other hand, when subjected to ultraviolet radiation, the lemon glycoside-supplemented section received scores better than those of the sample-free section in all the evaluation categories and the fermentation-treated aglycon-supplemented section received scores better than those of the lemon glycoside-supplemented section in all the evaluation categories and was shown to have inhibitory effect on the deterioration of flavor caused by ultraviolet radiation. The section supplemented with both fermentation-treated aglycon and vitamin C received scores equal to or better than those of the section supplemented with the fermentation-treated aglycon

TABLE 4

| Test condition | | Added concentration | Average score from sensory evaluation | | | |
|---|---|---|---|---|---|---|
| | | | Freshness | Juiciness | Intensity of flavor | Overall evaluation |
| Test 1-1 60° C. 4 days | Sample-free section | — | 2.0 | 2.2 | 2.1 | 2.1 |
| | Lemon glycoside | 30 ppm | 3.0 | 3.0 | 2.8 | 3.0 |
| | Aglycon | 30 ppm | 4.1 | 4.1 | 4.5 | 4.2 |
| | Aglycon Vitamin C | 30 ppm 30 ppm | 4.2 | 4.3 | 4.5 | 4.4 |
| Test 1-2 60° C. 4 days | Sample-free section | — | 2.2 | 2.4 | 2.4 | 2.4 |
| | Lemon glycoside | 3 ppm | 3.2 | 3.2 | 3.0 | 3.2 |
| | Aglycon | 3 ppm | 3.8 | 3.9 | 4.2 | 4.0 |
| | Aglycon Vitamin C | 3 ppm 3 ppm | 4.0 | 4.0 | 4.3 | 4.2 |
| Test 2-1 UV 6 hrs | Sample-free section | — | 2.0 | 2.2 | 2.1 | 2.2 |
| | Lemon glycoside | 30 ppm | 3.2 | 3.8 | 3.6 | 3.5 |
| | Aglycon | 30 ppm | 4.0 | 4.0 | 4.5 | 4.1 |
| | Aglycon Vitamin C | 30 ppm 30 ppm | 4.1 | 4.3 | 4.6 | 4.4 |
| Test 2-2 UV 6 hrs | Sample-free section | — | 2.4 | 2.5 | 2.4 | 2.6 |
| | Lemon glycoside | 3 ppm | 3.2 | 3.6 | 3.8 | 3.5 |
| | Aglycon | 3 ppm | 3.8 | 4.0 | 4.3 | 4.0 |
| | Aglycon Vitamin C | 3 ppm 3 ppm | 4.0 | 4.1 | 4.3 | 4.2 |

As seen in Table 4, when stored at a warmth of 60° C. for 4 days, the lemon glycoside-supplemented section received scores better than those of the sample-free section in all the evaluation categories, and the fermentation-treated aglycon-supplemented section received scores better than those of the lemon glycoside-supplemented section in all the evaluation categories and was rated as having remarkable effect in the intensity of flavor. The section supplemented with both fermentation-treated aglycon and vitamin C received scores better than those of the section supplemented with the fermentation-treated aglycon alone in all the evaluation categories in both Test 1-1 and Test 1-2. Although a sample-supplemented section with addition of the glycoside or the aglycon at a concentration of 1 ppm was evaluated in the same way, no alone in all the evaluation categories in both Test 2-1 and Test 2-2. These results showed that the addition of lemon aglycon at a concentration of 3 ppm or higher to the syrup solution exerted significant inhibitory effects on the deterioration of flavor caused by ultraviolet radiation.

When comparison was made between Test 1 and Test 2, there appeared a tendency to effectively suppress deterioration by ultraviolet radiation rather than by heating, although it depended on the test conditions. The panelists said in their replies that the sample-supplemented sections had a refreshing aftertaste as a whole. Thus, it was confirmed that the addition of vitamin C separately prepared to the fermentation-treated aglycon of Comparative Example 4 exhibited effects much higher than the total of their individual effects and produced a synergistic effect. When eriodictyol separately prepared is added to food or beverage containing vitamin C such as juice, it can easily be supposed that there is expected inhibitory effects on deterioration stronger than the inhibitory effects on deterioration expected from the amount of the eriodictyol added.

(Test of Inhibitory Effect on Fading of Pigment)

An aqueous solution adjusted to Brix 4.8 and pH 3.0 by use of glucose and citric acid was supplemented with 0.1% by weight of an anthocyanin pigment (red cabbage pigment) to prepare a syrup solution. A sample-supplemented or sample-free section of this syrup solution with or without addition of the fermentation-treated aglycon of Comparative Example 4 at an eriodictyol concentration of 30 ppm or both the aglycon and vitamin C was prepared. These sections were subjected to flash pasteurization by heating to 87° C. and then packed into clear, colorless PET bottles. Subsequently, a sample of each of these sections was irradiated with ultraviolet rays for 8 hours and then stored by refrigeration or stored by warming at 45° C. in the dark for 2 weeks. Absorbance at $\lambda$=460 nm was measured with a spectrophotometer (HITACHI spectrophotometer U2000) to determine a rate of the pigment remaining (%). The result is shown in Table 5.

TABLE 5

| | Added concentration | Percent of residual pigment (%) | |
|---|---|---|---|
| | | UV 8 hours | 45° C. 2 weeks |
| Sample-free section | — | 11.48 | 40.98 |
| Aglycon | 30 ppm | 41.81 | 67.23 |
| Aglycon | 30 ppm | 53.21 | 75.32 |
| Vitamin C | 30 ppm | | |

As seen in Table 5, inhibitory effects on the deterioration of natural pigment components extracted from vegetables, for example, anthocyanin and carotenoid, was improved by the addition of lemon aglycon and significantly improved by the addition of the lemon aglycon simultaneously with vitamin C. In addition, the effects were brought to the fore especially in ultraviolet irradiation and the fermentation-treated aglycon and vitamin C were useful for inhibiting the deterioration of natural coloring matter.

The invention claimed is:

1. A method for preparing an antioxidant material containing a flavonoid aglycon and vitamin C, wherein the flavonoid aglycon is eriodictyol and diosmetin, the method comprising:
   providing raw material containing eriocitrin and diosmin derived from lemons, limes, or sudachis; and
   treating the raw material with β-glycosidase derived from *Penicillium* multicolor to obtain the eriodictyol and diosmetin from the eriocitrin and diosmin in the raw material.

2. The method of claim 1, further comprising mixing the flavonoid aglycon obtained by treating the raw material with vitamin C.

3. The method of claim 2, wherein a rate of elimination of active oxygen during the treatment of the raw material is above 70%, thereby inhibiting deterioration of the antioxidant material.

4. The method of claim 1, wherein the treatment of the raw material is carried out at pH of 2.5 to 3.5.

5. The method of claim 1, wherein the treatment of the raw material is carried out at a temperature from 10° C. to 70° C.

6. A method for preparing an antioxidant material containing a flavonoid aglycon and vitamin C, wherein the flavonoid aglycon is eriodictyol and diosmetin, the method comprising:
   providing raw material containing eriocitrin and diosmin derived from lemons, limes or sudachis; and
   treating the raw material with an effective amount of β-glycosidase derived from *Penicillium* multicolor at a temperature from 20° C. to 40° C. to obtain the eriodictyol and diosmetin from the eriocitrin and diosmin in the raw material.

* * * * *